US006269846B1

(12) United States Patent
Overbeck et al.

(10) Patent No.: US 6,269,846 B1
(45) Date of Patent: *Aug. 7, 2001

(54) DEPOSITING FLUID SPECIMENS ON SUBSTRATES, RESULTING ORDERED ARRAYS, TECHNIQUES FOR DEPOSITION OF ARRAYS

(75) Inventors: James W. Overbeck, Hingham; Peter T. Flowers, Milton; Jean I. Montagu, Brookline; Myles L. Mace, Dover; Peter Honkanen, Arlington, all of MA (US)

(73) Assignee: Genetic Microsystems, Inc., Woburn, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/122,216

(22) Filed: Jul. 24, 1998

Related U.S. Application Data

(63) Continuation-in-part of application No. 09/006,344, filed on Jan. 13, 1998, and a continuation-in-part of application No. 09/045,547, filed on Mar. 20, 1998, and a continuation-in-part of application No. 09/079,324, filed on May 14, 1998, and a continuation-in-part of application No. 09/079,790, filed on May 15, 1998.

(51) Int. Cl.[7] .................................................. B05C 1/00
(52) U.S. Cl. ........................... 141/1; 422/100; 436/180; 118/243; 118/263; 427/256
(58) Field of Search ................... 141/1, 130; 222/583; 422/100; 436/180; 118/401, 243, 263; 427/256

(56) References Cited

U.S. PATENT DOCUMENTS 2,868,020   1/1959   Williams, Jr. ......................... 73/432

(List continued on next page.)

FOREIGN PATENT DOCUMENTS 0 373 203   6/1990   (EP).

(List continued on next page.)

OTHER PUBLICATIONS

Castellino, Alexander M.; "When the Chips are Down"; *Genome Research;* vol. 7, No. 10; (1997), pp 943–946.

(List continued on next page.)

*Primary Examiner*—Gregory L. Huson
*Assistant Examiner*—Peter deVore
(74) *Attorney, Agent, or Firm*—Philip L. McGarrigle; Alan B. Sherr; Ivan D. Zitkovsky

(57) ABSTRACT

A fluid deposit assembly mounted on a carrier for depositing minute drops of fluid at selected locations upon a substrate, comprising a deposit element having an exposed tip of diameter of 0.3 mm or less constructed and arranged to carry and deposit drops of fluid upon the substrate, stable lateral reference surfaces or surface portions exposed for engagement by the deposit element, the surfaces or surface portions being constructed and arranged to prevent X, Y displacement of the deposit element relative to the carrier when the deposit element is urged thereagainst and design for urging the deposit element against the reference surfaces or surface portions at least at the time that the deposit element approaches a substrate to deposit a fluid drop. The reference surfaces or surface portions and the design for urging are cooperating to precisely position the deposit tip in a precisely desired position as it contacts the substrate.

The deposit element is shown as the tip of an axially moveable pin. The reference surface portion is shown, among others, as a surface of revolution whose axis is disposed at a predetermined position relative to the carrier. A mobile supply in the form of a multiwell plate is moved under computer control to be a close companion of the deposit device, enabling rapid deposit action and avoidance of evaporative effects that can alter the consistency of dots in the array being formed. The device can deposit one dot on top of another from fluid in a mobile multiwell plate that moves to be close to the deposit device.

53 Claims, 18 Drawing Sheets

U.S. PATENT DOCUMENTS

| | | | |
|---|---|---|---|
| 3,329,964 | | 7/1967 | Mutschler et al. .................... 346/78 |
| 3,334,354 | | 8/1967 | Mutschler .......................... 346/140 |
| 3,356,462 | * | 12/1967 | Cooke et al. ....................... 422/102 |
| 3,568,735 | * | 3/1971 | Lancaster .......................... 141/238 |
| 4,041,995 | | 8/1977 | Columbus .......................... 141/275 |
| 4,096,825 | | 6/1978 | Golias et al. ....................... 118/221 |
| 4,142,656 | | 3/1979 | Smith et al. ........................ 222/325 |
| 4,322,063 | | 3/1982 | Fishbeck et al. .................... 267/160 |
| 4,340,390 | | 7/1982 | Collins et al. ....................... 23/230 |
| 4,387,384 | | 6/1983 | Sue ................................... 346/140 |
| 4,434,672 | | 3/1984 | Williamson et al. ............ 73/864.22 |
| 4,441,532 | | 4/1984 | Hrubesh ................................ 141/1 |
| 4,452,899 | | 6/1984 | Alston ................................. 436/46 |
| 4,567,585 | | 1/1986 | Gelbart .............................. 369/97 |
| 4,635,488 | | 1/1987 | Kremer ........................... 73/864.22 |
| 4,656,007 | | 4/1987 | Douchy et al. ....................... 422/64 |
| 4,659,677 | | 4/1987 | Glover et al. ....................... 436/174 |
| 4,737,344 | | 4/1988 | Koizumi et al. ..................... 422/100 |
| 4,981,783 | | 1/1991 | Augenlicht ............................ 435/6 |
| 5,186,982 | * | 2/1993 | Blette ................................. 427/256 |
| 5,202,231 | | 4/1993 | Drmanac ............................ 422/100 |
| 5,204,268 | | 4/1993 | Matsumoto .......................... 436/44 |
| 5,213,764 | | 5/1993 | Kerr et al. ........................... 422/100 |
| 5,223,225 | | 6/1993 | Gautsch ............................. 422/100 |
| 5,234,530 | * | 8/1993 | Freeman, III ...................... 156/358 |
| 5,262,128 | | 11/1993 | Leighton et al. .................... 422/100 |
| 5,306,510 | | 4/1994 | Meltzer ............................... 422/65 |
| 5,338,688 | | 8/1994 | Deeg et al. ......................... 436/180 |
| 5,344,666 | | 9/1994 | Levine ............................. 427/2.11 |
| 5,428,690 | | 6/1995 | Bacus et al. ........................ 382/128 |
| 5,436,129 | | 7/1995 | Stapleton .............................. 435/6 |
| 5,443,791 | | 8/1995 | Cathcart et al. ..................... 422/65 |
| 5,492,806 | | 2/1996 | Drmanac et al. ....................... 435/5 |
| 5,525,464 | | 6/1996 | Drmanac et al. ....................... 435/6 |
| 5,540,891 | | 7/1996 | Portmann et al. ................... 422/102 |
| 5,551,487 | | 9/1996 | Gordon et al. ......................... 141/1 |
| 5,607,861 | | 3/1997 | Komatsu et al. .................... 436/50 |
| 5,626,740 | | 5/1997 | Seto et al. .......................... 205/789 |
| 5,665,312 | | 9/1997 | Sperber et al. ...................... 422/81 |
| 5,700,637 | | 12/1997 | Southern et al. . | 
| 5,756,050 | | 5/1998 | Ershow et al. .................... 422/100 |
| 5,770,151 | | 6/1998 | Roach et al. ........................ 422/63 |
| 5,800,992 | | 9/1998 | Fodor et al. ............................ 435/6 |
| 5,807,522 | | 9/1998 | Brown et al. ....................... 422/50 |
| 5,834,062 | * | 11/1998 | Johnson et al. .................... 427/256 |
| 5,882,930 | | 3/1999 | Baier .................................. 436/49 |
| 5,895,630 | | 4/1999 | Skaborn et al. .................... 422/100 |
| 5,939,022 | * | 8/1999 | Franciskovich .................... 422/100 |

FOREIGN PATENT DOCUMENTS

WO 95/04594   2/1995  (WO) .

WO 95/09248   4/1995  (WO) .

OTHER PUBLICATIONS

Ekins, R.P., et al., "Multianalyte Immunoassay: The Immunological "Compact Disk" of the Future"; *Journal of Clinical Immunoassay;* vol. 13, No. 4; (1990), pp 169–181.

NORMAG, Northern Magnetics Inc., company brochure.

NORMAG, "Single Axis High Performance Linear Stepper Motors", product description, pp 1.

"The Perfect Solution for Your Testing Problem", © Ostby Barton, (1997); product description, pp 1.

BioRobotics, "The MicroGrid", product description, pp 2.

"Gridding & Replicating Application", Revised: Nov. 1997 © *PBA Technology Ltd.,* pp 1–2.

Geysen, H. M., et al.; "Strategies for epitope analysis using peptide synthesis"; *Journal of Immunological Methods;* vol. 102; (1987), pp 259–274.

Graves, David J., et al.; "System for Preparing Microhybridization Arrays on Glass Slides"; *Analytical Chemistry;* vol. 70, (1998) pp 5085–5092.

Kalachikov, S., et al.; Colony Selection with an Automated 383–Pin High–Density Replicating Tool (HDRT); BioRobotics, ©1996 Beckman Instruments, Inc.; pp 1–7.

Lemieux, B., et al.; "Overview of DNA chip technology"; *Molecular Breeding;* vol. 4, (1998); pp 277–289.

Pease et al; "Light–generated oligonucleotide arrays for rapid DNA sequence analysis"; *Proc. Natl. Acad. Sci. USA;* vol. 91, pp. 5022–5026, May 1994.

Southern et al.; "Molecular interactions on microarrays"; The Chipping Forecast; *Nature Genetics;* vol. 21, pp. 5–9; Jan. 1999.

Trent et al., "Workshop on Methods and Applications of DNA Microarray Technology"; Jan. 11–13, 1998.

"Microfiltration Apparatus"; *Chromatography Electrophoresis Immunochemistry Molecular Biology HPLC;* catalogue M 1987.

Hames et al.; "Nucleic Acid Hybridization: A Practical Approach"; *IRL Press* Oxford England; 1985.

"BioRobotics Latest Developments"; Robotics, Beckman Instruments, Inc.; 1997.

Abstracts of papers presented at the 1994 meeting on Genome Mapping & Sequencing; pp. 48, 60–62, 198, 203, 296–297; May 11–15, 1994.

Gilson; "Raising The Speed Limit On Liquid Handling . . . Again!" advertisement p 1.

* cited by examiner

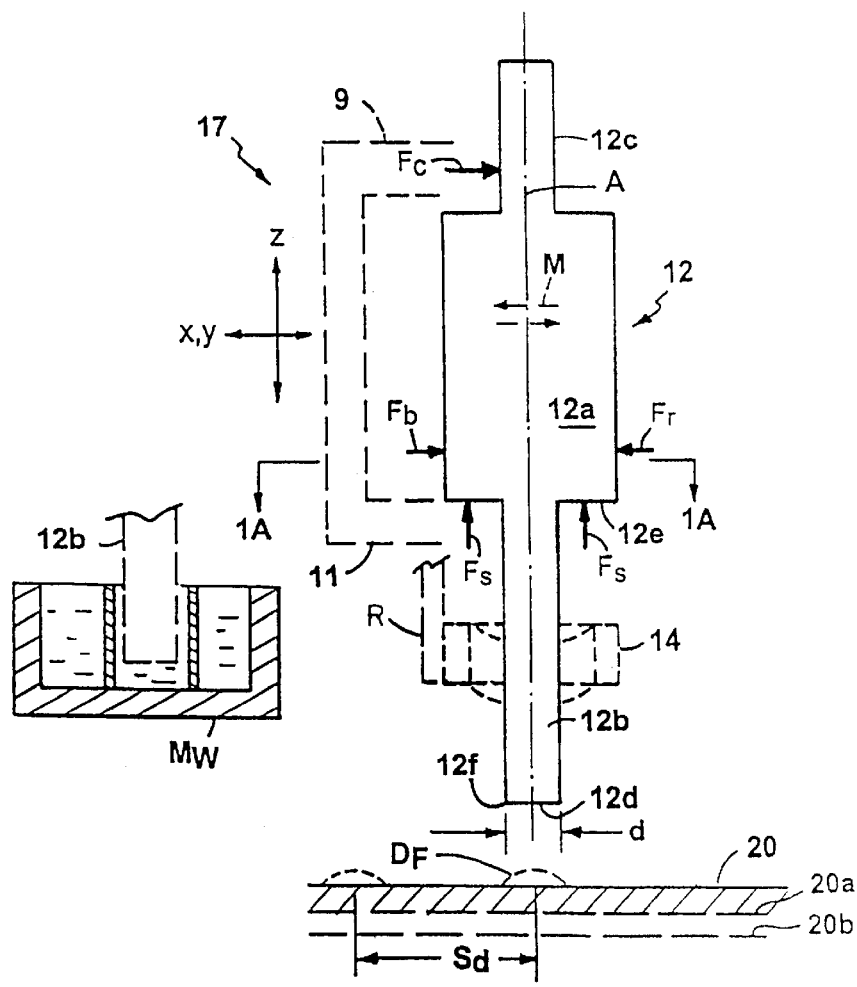
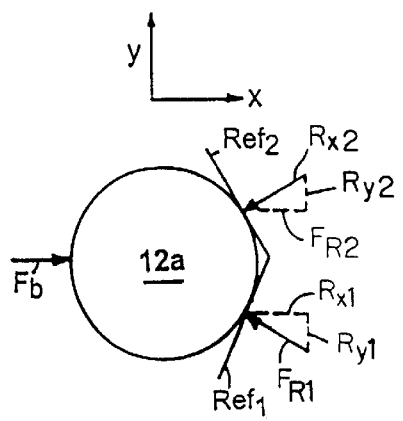
FIG. 1
FIG. 1A

FIG. 1B          FIG. 1C

```
            A B C D E F G H
          1  ○ ○       ○ ○ ○ ○
          2  ◎ ◎ ◎ ◎ ○    Pins Supplied by
          3  ◎ ◎ ◎ ◎ ○    96 well plate
          4  ◎ ◎ ◎ ◎ ○
          5  ○ ○ ○ ○ ○ ○ ○ ○
          6  ○ ○ ○ ○ ○ ○ ○ ○
          7  ○ ○ ○ ○ ○ ○ ○ ○
          8  ○ ○ ○ ○ ○ ○ ○ ○
          9  ○ ○ ○ ○ ○ ○ ○ ○
         10  ○ ○ ○ ○ ○ ○ ○ ○
         11  ○ ○ ○ ○ ○ ○ ○ ○
         12  ○ ○ ○ ○ ○ ○ ○ ○
```

The pin assembly follows
the pattern for supply:

pin 1 → R1  COL A
        R1  COL C
        R1  COL E
        R1  COL G
        R5  COL A
        R5  COL C
        R5  COL E
        R5  COL G
        R9  COL A
        R9  COL C
        R9  COL E
        R9  COL G

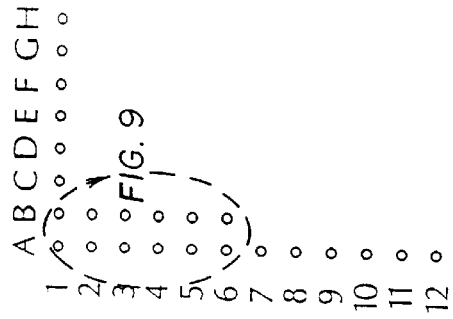
*FIG. 10*
The pin assembly
follows the pattern
COL A    ROW 1
COL C    ROW 1
COL E    ROW 1
COL G    ROW 1
COL A    ROW 7
COL C    ROW 7
COL E    ROW 7
COL G    ROW 7
*FIG. 11*
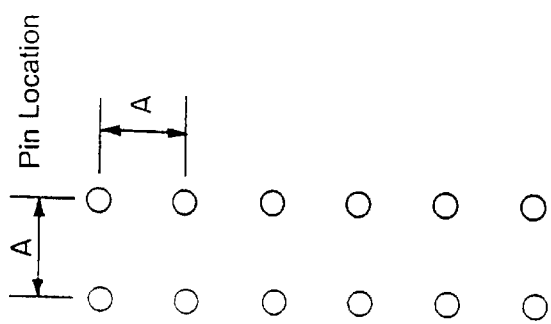
*FIG. 9*

DEPOSITING FLUID SPECIMENS ON SUBSTRATES, RESULTING ORDERED ARRAYS, TECHNIQUES FOR DEPOSITION OF ARRAYS

RELATED APPLICATIONS

This application is a continuation in part of U.S. patent application Ser. No. 09/006,344, filed Jan. 13, 1998, entitled "Depositing Fluid Specimens on Substrates", of U.S. patent application Ser. No. 09/045,547, filed Mar. 20, 1998, entitled "Wide Field of View and High Speed Scanning Microscopy", of U.S. patent application Ser. No. 09/079,324, filed May 14, 1998, entitled "Depositing Fluid Specimens On Substrates, Resulting Ordered Arrays, and Techniques For Analysis of Deposited Arrays, and of U.S. patent application Ser. No. 09/079,790, filed May 15, 1998, entitled "Focusing in Microscope Systems", each of which is hereby incorporated fully by reference as if it were an integrated part of this application.

FIELD OF INVENTION

Well developed biological analytical technology, as well as recently developed "Lab on a Chip" or "Gene Chip" techniques require creation of dense arrays of fluorescently labeled micro-organisms and DNA assays in a two dimensional field. It is desirable to place the arrays on a conventional microscope slide, and to create many such slides simultaneously in a manufacturing process.

In important applications, single stranded DNA or PNA or other biological elements in the form of fragments carrying known information are distributed onto the surface of a planar field array containing up to possibly 100,000 objects per microscope slide. The objects of the array represent discriminating sequence information. Different laboratories have targeted the objects of the array to have various spot sizes over a range of the order of 25 to 250 $\mu$m in diameter, depending primarily upon the total number of objects anticipated in the array. The objects of the array are probed with fluorescently labeled fragments of potential complementarily. When a match occurs between these fragments and hybridization occurs, a positive is scored by observing fluorescence at the site of hybridization. By manipulating the deposition of complementary strands or fragments into the array and scoring "hits", many levels of information can be inferred.

For gene chip technology to proceed to complete fruition, as well as to improve the application of previous analytical techniques, economical instruments have been needed that can rapidly and accurately create the dense array of objects over a large field portion of a glass microscope slide that occupies approximately 22 mm wide and 50 mm long of a slide that is nominally 25 mm×75 mm.

In the deposition upon a microscope slide of discrete, minute quantities of a large variety of fluid materials, the volume deposited at a discrete spot typically may be from a few pico liter to a fraction of a micro liter, depending upon the application. The biological material carried in this fluid can range from a few strands of short oligonucleotides in a water solution to a high concentration of long strands of complex proteins. The properties of these fluids vary enormously. Some are akin to water while others are far more viscous, resembling a light oil or honey. The range of fluids that may be employed also exhibits wide differences in evaporative characteristics and in other properties.

Such large range of property variations in fluids of interest has caused great difficulties for any single type of process to operate over a wide range.

Certain processes employing photolithographic techniques have offered excellent positional accuracy of the objects and high dot density but have great limitations due to cost and due to the limited range of biological and chemical techniques that are applicable. These techniques typically construct short segments of DNA or other molecules by adding single bases, one at a time.

Certain other processes for forming arrays of dots of biological material have utilized piezo micro cylinders to aspirate and jet small volumes of fluid containing the material while others have used processes akin to a fountain pen, comprising a "quill" deposition tool. An assemblage of quills suck up a desired amount of fluid and by tapping a quill upon the receiving substrate, the meniscus holding the fluid in the gap of the quill breaks, due to inertia of the fluid within the suddenly stopped tool, so that a drop of fluid is effectively propelled from inside the quill to the impacted surface.

The development of such techniques has occurred against the background of the quite old technique for forming much larger deposits, of transferring a portion of fluid by a pin or a set of pins that are e.g. dipped in a fixed reservoir containing fluid to be transferred and moving the pins into position to contact a usually soft substrate to form relatively large spots. Some of these instruments are known as "replicators". An example of a product produced by such prior pins would be a 22 cm×22 cm bioassy plate carrying 0.6 mm diameter spots located on a grid 1 mm on center. This spot density is approximately 3 orders of magnitude too low from that needed for current "Gene Chip" applications, and the previously known techniques are impractical for present purposes for a number of other reasons as well.

SUMMARY OF THE INVENTION

Our purpose is to provide a technology adapted to the deposition of very small drops of fluids, e.g. drops that form spots of less than about 300 $\mu$m diameter, and in important cases much smaller than that, and at high density, the fluids and the resultant spots permissibly exhibiting a wide range of properties such as viscosity, evaporative characteristics, surface tension, wettability, surfactant characteristic, dynamic contact angle and free surface energy. The present invention employs features presented in U.S. patent application Ser. No. 09/006,344, filed Jan. 13, 1998, entitled "Depositing Fluid Specimens on Substrates" and in our further applications referred to above, as well as additional technology, to be described below.

A. Features Described in our Prior Applications

In our U.S. applications Ser. No. 09/006,344 and U.S. Ser. No. 09/079,324 we describe apparatus for deposit of fluid samples in a dense array of mutually isolated dots, comprising a deposit pin or other deposit device, a fluid source for repeatedly providing a dot of fluid on the end of the deposit pin or device, mechanism for moving the pin or device relatively over an array of spaced apart deposit locations of a receiving substrate, mechanism for repeatedly moving the pin or device, relatively, toward and away from the receiving substrate to deposit respective dots at respective deposit locations on the substrate, a cleaning system, and a control system adapted to control relative movement of the deposit pin or device between a resupply relationship to the source, a depositing relationship to the substrate over the array of spaced apart deposit locations on the substrate, and a cleaning relationship to the cleaning system mechanism.

In preferred embodiments the deposit device has a tip of diameter of about 0.3 mm or less, and is so constructed and constrained in space that the tip is compliant axially while being precisely located laterally relative to the receiving substrate. (By "compliant" is meant that the tip has a range of movement in the absence of a substrate, but stops wherever the substrate may lie within the range, the tip readily stopping when it encounters the substrate, without exertion of significant force or impact energy by the tip on the substrate).

Also in our prior application we have shown a moveable deposit device associated with a local fluid storage device that is separate from but generally moveable with the deposit device over the array of deposit locations, the fluid storage device being constructed and arranged to locally resupply the deposit device during its deposit sequence.

In certain cases shown, the local storage device is constructed and arranged to be replenished from a remotely located relatively large reservoir, the reservoir being constructed to store a multiplicity of isolated fluid volumes, the apparatus constructed to move the local supply device to a selected fluid volume of the reservoir for replenishment.

In these arrangements the deposit device can quickly pick up a drop of fluid from its companion mobile supply without excessive movement, and then can deposit the drop fully as an accurately located, small dot deposit, without influence by the fluid supply.

In our prior applications, for use in certain cases, we employ a mobile supply member in which a pin or other device is dipped. In other advantageous cases a member defines a generally annular fluid retention surface and a deposit pin or other deposit device is constructed to move within the annular retention surface from retracted to extended positions. In the retracted position the deposit portion of the deposit device is retracted from the lower surface of fluid retained by the annular surface of the storage device, and in the extended position the deposit portion is projected beyond the lower surface of the retained fluid, to pick up and carry a precisely sized small drop of fluid to the substrate surface.

In certain embodiments of that feature, a plurality of pins, e.g., four pins, are mounted on a deposit head that translates over an array of slides, each pin being associated with an independently controlled driver, and a discrete local fluid supply is provided for each respective pin, the supplies constructed to be replenished independently from each other. Ganged operation of a number of deposit devices according to principles of the invention are also explained.

Numerous other useful and important features are shown in our prior applications, to which the reader is referred, all features of these applications being incorporated here by reference.

B. Further Features

Here we provide further general features, and specific embodiments of those features, that are simple and well suited to accomplishing repeatable positioning of a small fluid deposit tip, i.e. a microtip, with high accuracy, to produce arrays of small spots at high density. One aspect concerns the general principle, in an array for forming tiny dots, of causing deposit element, for instance a pin, the tip of which is very small and axially compliant, to engage lateral reference surfaces that are so related as to ensure the repeatability of the X, Y position of the tip.

In preferred embodiments the deposit element is a pin which is biased lightly by gravity action or spring force or magnetic or electrostatic forces against the lateral reference surfaces, the pin being free to move bodily, in the direction of its long axis, to provide tip compliance.

In certain preferred embodiments a pin shaft has a form that seats in a plate that has a mating shape having a component of extent that provides lateral confinement, under conditions in which the pin is biased to one side of that shape. Suitable complementary shapes are typically surfaces that curve about axes substantially normal to the substrate, e.g. surfaces of revolution that include a sphere and a cone or two cones or a cone and a hole. Provisions that prevent rotation of the pin are preferably included.

According to one aspect of the invention, a fluid deposit assembly is mounted on a carrier for depositing minute drops of fluid at selected locations upon a substrate, comprising a deposit element having an exposed tip of diameter of 0.3 mm or less constructed and arranged to carry and deposit drops of fluid upon the substrate, stable lateral reference surfaces or surface portions are exposed for engagement by the deposit element, the surfaces or surface portions constructed and arranged to prevent X, Y displacement of the deposit element relative to the carrier when the deposit element is urged thereagainst and means for urging the deposit element against the reference surfaces or surface portions at least at the time that the deposit element approaches a substrate to deposit a fluid drop, the reference surfaces or surface portions and the means for urging cooperating to precisely position the deposit tip in a precisely desired position as it contacts the substrate.

Preferred embodiments of this aspect of the invention have one or more of the following features.

The deposit element of the fluid deposit assembly is the tip of an axially moveable pin.

The means for urging comprises a spring having spring properties selected to provide compliance to the tip of the pin.

Preferably, a spring provides at least in part the pressure with which the pin bears upon the substrate.

The means urging the deposit element comprises an arrangement of the assembly so that gravity effects cause the deposit element to engage the reference surfaces or surface portions. In certain cases the deposit device is tilted in a manner by which gravity acting upon the device produces the engagement, and in particular cases an eccentric weight acts through the device to maintain the engagement.

The reference surface portion of the deposit assembly comprises a surface of revolution whose axis is disposed at a predetermined position relative to the carrier. In certain cases the surface of revolution is in the form of a circular supporting ledge that supports the element from moving in its assembly in the direction toward the substrate, but from which the element is free to lift off in response to contact of the tip with the substrate as the ledge and elongated element are together moved relatively toward the substrate.

A resilient member urges the deposit element into engagement with a reference in the form of a surface of revolution. In certain cases the surface of revolution has a surface of form substantially matching the form of the portion of the element disposed to engage the surface of revolution. The surfaces are respectively concave and convex conical, each conforming to a portion of the surface of a right cone or the surface of revolution is of concave curvature and the mating surface of the deposit element is of convex curvature.

The means for urging the deposit element comprises a spring arranged to urge the deposit element substantially axially. The means for urging the deposit element applies a turning moment on the deposit element. In certain cases the deposit element is elongated, the moment is applied by a pushing member engaged with a remote end of the deposit element, one of the engaged end and a pushing surface comprises a surface set at an acute angle to the long axis of the elongated element, and the other of the surfaces comprises a convexly curved surface engaged upon the angled surface. In certain cases a confined ball is pushed toward the inclined surface.

A formation on a part of the deposit element engages a mating formation on the carrier to prevent rotation of the element.

The end of the deposit tip is of substantially square side profile adapted to carry fluid by surface tension effects.

A deposit assembly comprises a multiplicity of the deposit devices mounted for motion together in response to a common actuator. In certain cases the deposit devices are deposit pins. In certain cases the spacing of the devices corresponds to the spacing of wells of a predetermined multiwell plate, in certain preferred cases the spacing corresponds to the well-to-well spacing of wells of a 96, 384, 864 or 1536 well plate.

The assembly is combined with a mobile fluid supply that is constructed to accompany the deposit device across the substrate.

The assembly is combined with a fluid carrier ring that has a surface energy greater than about 2500 mN/m, in certain cases the surface comprising tungsten.

The tip of the deposit element has a surface energy greater than about 2500 mN/m, in certain cases the surface of the tip of the deposit element comprises tungsten.

The fluid deposit assembly is incorporated into an apparatus for deposit of fluid samples in a dense array of mutually isolated dots, comprising a deposit device in the form of the fluid deposit assembly as described above, a fluid source for repeatedly providing a discrete dot of fluid on the tip of the deposit element of the device, mechanism for moving the device relatively over an array of spaced apart deposit locations of a receiving substrate, mechanism for repeatedly moving the device, relatively, toward and away from the receiving substrate to deposit respective dots at respective deposit locations on the substrate. In certain preferred cases there are included a cleaning system and a control system adapted to control relative movement of the deposit device to a depositing relationship to the substrate and a cleaning relationship to the cleaning system.

In certain cases the fluid source includes a fluid storage device relative to which the storage device repeatedly moves to resupply the device during the deposit of successive dots. In certain case the fluid storage device is a local fluid storage device separate from the deposit device and generally movable over the array of deposit locations, the fluid storage device being constructed and arranged to resupply the deposit device at various locations with respect to the array.

Another aspect of the invention is a deposit device such as a pin constructed and arranged to dip into a volume of fluid carried by a mobile local storage device, that moves as a companion to the storage device, the mobile local storage device being constructed to store a multiplicity of isolated fluid volumes, the apparatus constructed to move the local supply device relative to the deposit device to select the fluid to be deposited. In certain advantageous cases the storage device is a plate having 96 wells or multiples of 96 wells.

The deposit device is preferably a moveable pin having some of the features that have been previously described and a local storage device includes a member which defines a generally annular fluid retention surface, and the deposit pin is constructed to move within the annular retention surface from retracted to extended positions, in the retracted position the deposit end of the pin being retracted from the lower surface of fluid retained by the annular surface of the storage device, and in the extended position the deposit end of the pin being projected beyond the lower surface of the retained fluid. In certain cases preferably the annular surface is aligned with the pin and a driver is associated with the member that defines the annular surface to move the member generally linearly downwardly beyond a position of a deposit end of the pin to a replenishment position, the pin and the member defining the annular surface and associated drivers being movable to the cleaning system, and to a replenishment region in which the annular member is replenished.

According to another aspect of the invention, a method of producing arrays of fluid dots comprises providing an array of pickup pins having pin spacing comparable with the well spacing of a 96 well plate, or a plate having a multiple of 96 wells, dipping the pickup pins into wells of the well plate with which the device is registered and transferring the dots on respective pickup devices to respective dot locations in a substantially denser array on a substrate. Preferably the well plate is mobile and accessible to the pickup pins and is controlled to stay close to the regions in which the pins are depositing their fluid.

According to another aspect of the invention an array product comprising deposited dots of fluid in an array corresponding to a function of the distribution of wells of a 96 well plate.

BRIEF DESCRIPTION OF DRAWINGS

FIG. 1 is a free body diagram of a deposit pin, also illustrating mobile reservoirs with which it is employed.

FIG. 1A is a cross-section taken on line 1A—1A on FIG. 1.

FIGS. 1B and 1C are views similar to FIG. 1A illustrating respective arrangements for applying a side load to a deposit pin.

FIG. 1D is a diagrammatic perspective view of a pin that has a conical seating surface mated with a complementary conical seating surface of a support plate, while

FIG. 1G is a magnified view of a pin and ring assembly in which the fluid contact surfaces are specially coated while

FIGS. 2, 2A, 2B and 3 are diagrammatic side views of alternate forms of deposit pins while

FIG. 4 is a perspective view of a multi pin deposit head mounted for cooperation with a multiwell mobile supply reservoir while

FIG. 5 is a diagram of an operable pin pattern of eight micro deposit pins while FIG. 6 illustrates the initial relationship of the pins to a standard 96 well supply plate.

FIG. 7 defines a useful sampling sequence for the pins of FIG. 5 and

FIGS. 9, 10, 11, 12 and 12A are views similar, respectively, to FIGS. 5–8, illustrating an arrangement employing a 12 pin pickup array used with a 96 well supply plate.

FIG. 14 is a perspective of the device of FIG. 13B mounted for X,Y and Z travel as an array-forming device while

DESCRIPTION OF PREFERRED EMBODIMENTS

Figure 1D:
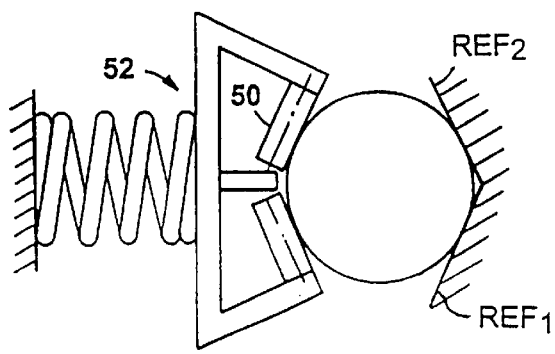
Figure 1D:
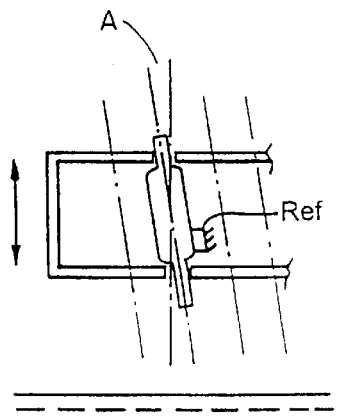
Figure 1D:
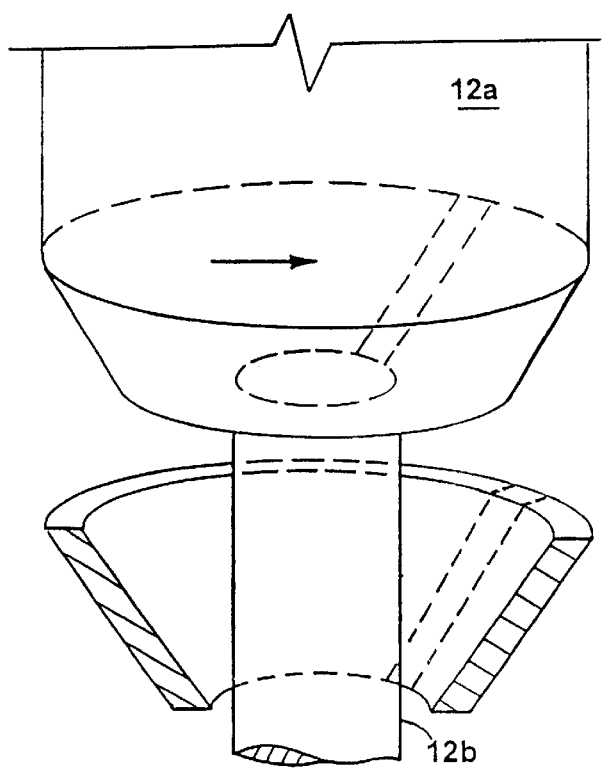

FIG. 1 is a free body diagram of a deposit pin 12 in an assembly that achieves precise, compliant X,Y positioning of its micro tip. The tip 12d is of diameter d less than about 0.3 mm, preferably in a range between about 0.250 mm and 0.025 mm, and is capable of depositing micro dots of fluid of corresponding dimension in a tightly packed array upon a rigid substrate.

In the arrays, typically the center-to-center spacing between dots, $S_d$, is no more than three times the diameter of the dots and often only twice or one and a half times the diameter. Thus it is understood that dots of diameter between 0.25 mm and 0.025 mm, at center to center spacings between about 0.750 to 0.500 mm for the larger dot and 0.075 mm and 0.050 mm or less for the smallest dots result in a wide range of density of dots, that can be characterized as "high density" to "ultra high density", which are all capable of being produced by the principles described here.

The pin comprises a relatively large body 12a and a lower portion 12b of reduced dimension that leads to micro deposit tip 12d. The pin also has an upper guide portion 12c.

Large body 12a provides a downwardly-directed surface 12e that is engaged upon a support, receiving support force $F_s$ that bears the pin's weight.

The assembly is constructed to enable a lateral bias force $F_b$ to urge pin 12 against a pair of reference surfaces $Ref_1$, and $Ref_2$ which lie at an angle to each other, as viewed in horizontal cross-section, FIG. 1A. These reference surfaces are arranged to resist movement of the pin in X and Y coordinates by applying reaction forces that have X and Y components that balance bias force $F_b$. The reference surfaces are constructed to leave the pin free to move axially along axis A (Z direction) to provide compliance to the tip 12d when the substrate S is encountered.

In practical embodiments for mounting the pins it is advantageous to employ two vertically spaced horizontal plates 9 and 11 shown in dashed lines, joined to form a carrier 17 that moves in X,Y and Z directions for carrying the pin through deposit, cleaning and resupply positions. The upper plate 11 is disposed at a selected distance from the lower plate and applies a constraining force $F_c$ to constrain the angle of the pin, and hence the position of its tip 12d, within selected tolerance.

Lowering carrier 17 causes the precisely positioned tip 12d to engage the substrate S, whether the substrate be found at position 20, 20a or 20b, over the design range. Upon engagement with the substrate the pin stops. Further downward movement of the carrier causes the pin to be lifted from its seat, while reverse movement causes the pin to reseat.

The bias force $F_b$ is applied by structure or arrangement that preferably permits free axial movement of the pin relative to its carrier, in response to the tip encountering the substrate. FIG. 1B illustrates application of lateral force by miniature spring-loaded bearings that urge the pin toward an inside corner defined by the reference surfaces $Ref_1$ and $Ref_2$. In this particular case miniature rollers 50 carried on structure 52, turn with axial motion of the pin. In other cases ball bearings may be employed. FIG. 1C illustrates tilting the longitudinal axis A of the pin in a manner that the weight of the pin applies to itself a slight turning moment that biases the pin against reference surfaces $Ref_1$ and $Ref_2$.

Figure 1E:
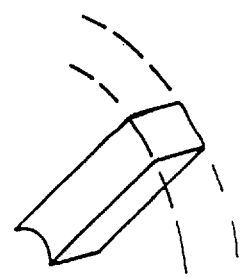
FIG. 1E is a diagram of a longitudinal segment of the support seat and FIG. 1F is a plan view analyzing reaction forces of the support seat in response to a lateral biasing force applied to the pin.
Figure 1F:
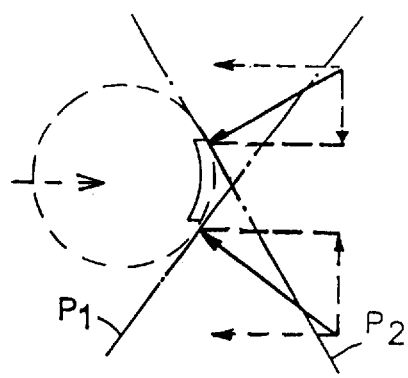

FIGS. 1D, 1E and 1F show that tangent planes $P_1$ and $P_2$ to a segment of a conical seat (FIG. 1E) against which a pin is engaged can be considered to define two reference surfaces set at an angle to one another, that act in the manner as explained in FIG. 1 to resist lateral movement of the pin in both X and Y directions. The same is true more broadly, encompassing other surfaces of revolution that define seating surfaces. Preferential seating upon a given segment of such a seat may be achieved by selected loading techniques described.

In FIG. 1 mobile multiwell reservoir MW is shown associated with the pin. It moves over the substrate during the deposition action to be near the deposit pin as the pin progressively forms dots upon the substrate, the pin resupplying itself from the reservoir MW for each dot by small motions that limit evaporation.

In FIG. 1, by dotted lines, also shown is an alternative local mobile reservoir in the form of a fluid carrying ring 14 through which the pin can project as described in our prior applications, with the actions and advantages as described there.

Figure 1G:
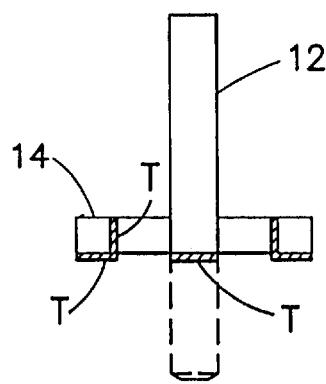
Figure 1H:
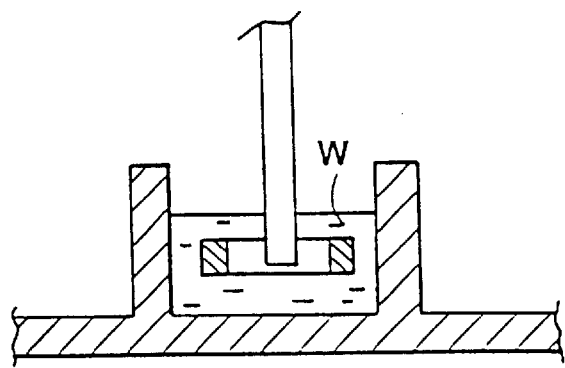
FIG. 1h illustrates on a less magnified scale the immersion of the assembly for pickup of a local fluid supply and FIG. 1i, similar to FIG. 1h, illustrates the fluid load that is picked up by the assembly.
Figure 1I:
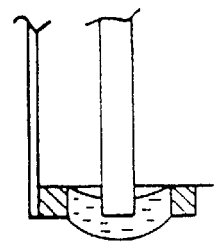

In FIG. 1G is shown a preferred form of pin and ring assembly in which fluid contacting surfaces of both ring 14 and pin 12 are defined by a substance having a surface energy in excess of 2500 millinewton per meter (mN/m), in this preferred embodiment the surfaces being defined by electroplated tungsten layers T. Also shown in FIG. 1G is an advantageous relationship of pin and ring at the time the ring is resupplied. Referring to FIG. 1H, at the time of immersion of the ring in a selected well W of a multiwell plate, the presence of the pin within the confines of the ring helps the ring pick up the fluid by surface tension effects that effectively compete with the surface tension effects of the well itself, which tend to resist removal of small quantities of fluid. In the presently preferred relationship, the bottom tip surface of the pin is aligned with the lower surface of the ring. Thus, referring to FIG. 1I, withdrawal of the assembly from immersion in the well W results in withdrawing a desired amount of fluid, pendent as a large meniscal drop, bounded by the pick up ring this quantity, protected by the ring is then available for deposit in tiny drops by repeated projection of the pin downward form the ring, see dotted lines in FIG. 1G.

Figure 2:
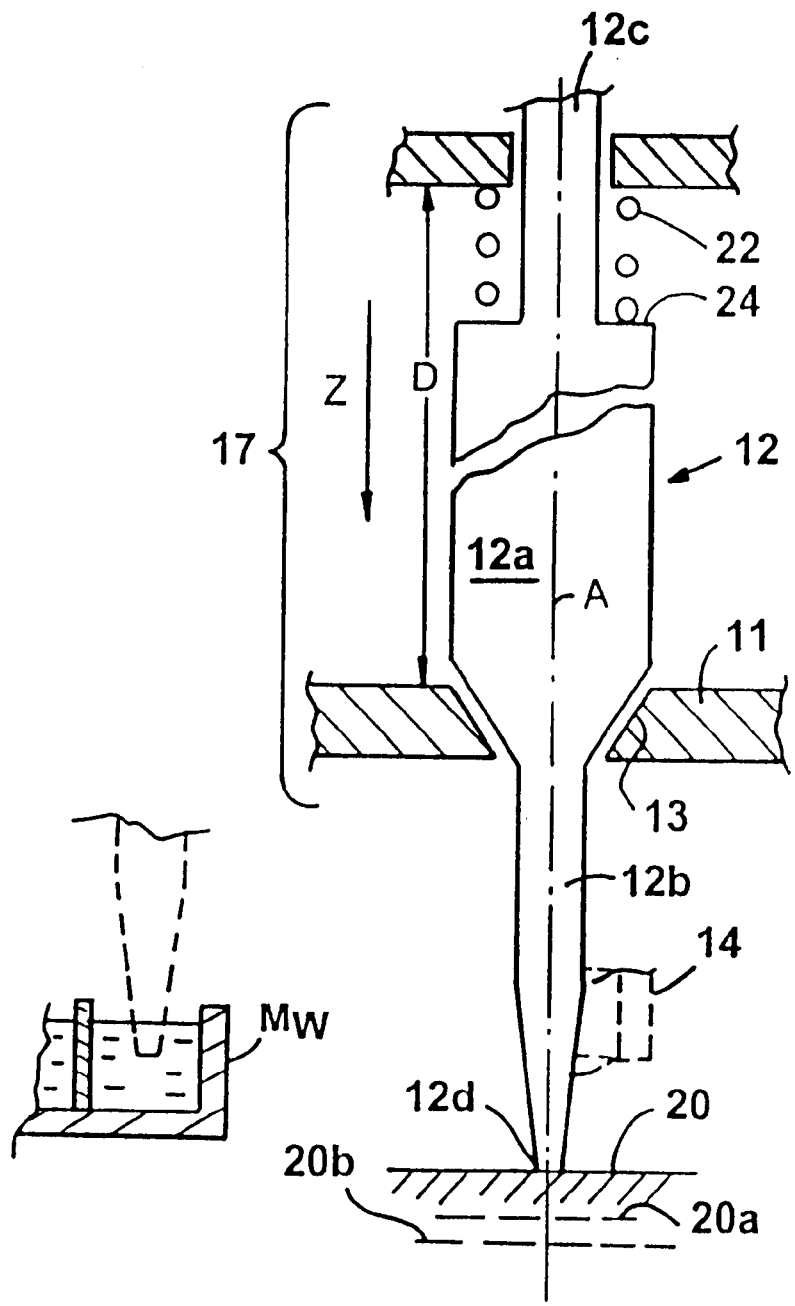
Figure 2A:
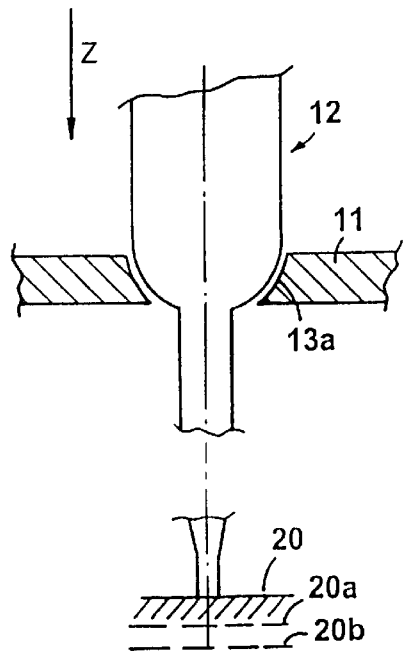
Figure 2B:
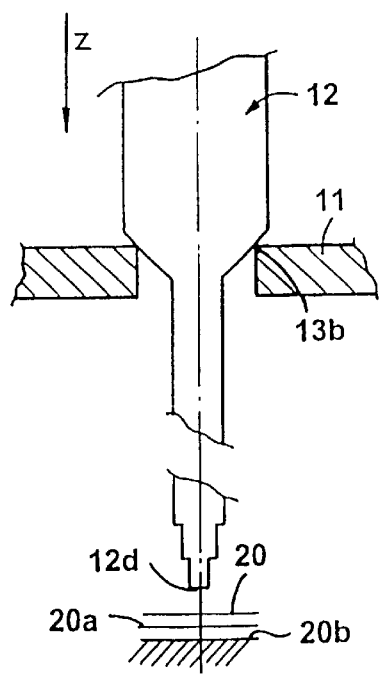

Referring now to FIGS. 2, 2A and 2B, embodiments employing a surface of revolution for seating the pin are exemplified. Fluid deposit pin 12, (associated with a fluid supply such as mobile multiwell plate MW or an associated supply ring 14), is constrained between upper and lower plates 9 and 11. These plates define a carrier 17 that moves as a unit in the direction of arrow Z for supply and deposit actions. In each case, an enlarged portion of the pin 12a rests normally in a seat which bears the weight of the pin, the pin being free to be displaced relatively upwardly from its seat upon contact of the tip with substrate 20. When the pin 12 rests in its seat 13, 13a or 13b, in lower plate 11, the X,Y position of its tip 12d is defined by the degree of perfection of the pin 12, the relative distance to the upper supporting plate 9, the clearance between upper portion 12c of the guide pin and the guide hole 17, in that plate in which it resides, and a feature in the system that applies a definite (though permissibly slight) bias of the pin to a given side of the engaging structure as has been described above. In FIG. 2 compression spring 22 is disposed between upper plate 9 and upwardly directed ledge 24 of pin 12. The spring is fixed in position and applies its downward force with slight and predictable asymmetry relative to center axis A, to bias the pin to a given side for repeatable positioning. Spring 22 is sized and arranged to provide the correct deposition pressure of the tip 12D of the pin on the substrate 20 in cases where the mass of the pin is insufficient; concurrently the slight non axi-symmetric effect of this spring introduces the desired lateral bias.

In the arrangements of FIGS. 2A and 2B the pin is biased laterally, e.g. employing one of the systems previously described, e.g. by use of a spring, angling the axis of the pin a few degrees from vertical (with the axes of all adjacent pins being parallel when an array of pins is employed), or by introducing bias by an eccentric load or by other loading techniques. In the case of magnetics, magnetic attraction can be employed to draw the pin to a defined corner or a particular arc of a conical seat. Permanent magnets or electromagnets may be employed. Likewise, electrostatic forces can be employed by imparting a charge to one of the members relative to the other, and employing a dielectric layer to prevent discharge of the charge so that the attraction persists at the time of approach of a deposit down towards the substrate.

The pin of FIGS. 2, 2A or 2B is readily formable to a high degree of perfection, for instance of cylindrical form. The distance D is readily selectable, in view of the fact that for a given clearance allowance between the hole of the upper plate and upper pin portion 12c, increase of distance D decreases the possible disturbance of the pin from its nominal orientation due to any variation in clearance.

Thus, the bottom plate 11 defines the position of the tip of the pin 12d, the top plate 9 being located sufficiently remotely that the spacing and angles produced establish the position of the tip of the pin within desired close tolerances for deposit of dense arrays on the surface of substrate 20.

It is seen from FIGS. 2, 2A and 2B that the driven carrier structure 17 for the pin is arranged to travel sufficiently to ensure that micro tip 12d can reach the lowest level 20b of the range of permissible substrate heights, whereas the tip 12d is compliant in the sense that the pin can yield in position and exerts only a controlled light pressure on the substrate before it lifts from its seat wherever it encounters the substrate over the design range.

Figure 3:
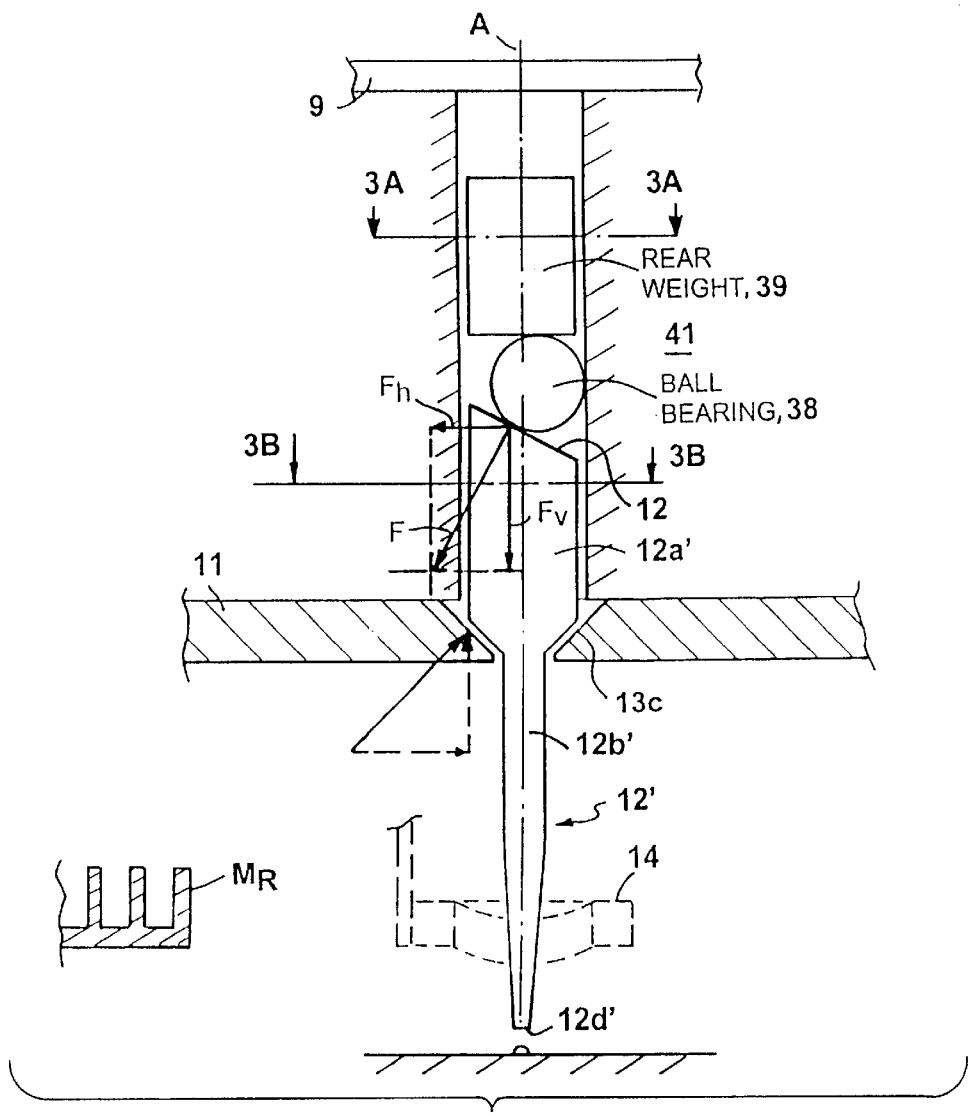

In FIG. 3, pin 121 and seat 13c have complementary conical seating surfaces. The upper end 12f of the enlarged body portion 12a' is sloped in a selected direction explained further below and a ball bearing 38 bears on the sloped surface at a point offset from central axis A. A weight 39 rests upon the ball, being housed by a bore in spacer block 41 upon which the upper and lower plates 9 and 11 are affixed. The spacer block is advantageously of a low-friction engineering plastic such as Delryn. The weight 39 is of selected size to adjust the degree of compliance desired for the deposit tip 12d and to apply, via the eccentrically located ball, a turning moment M to the pin (see FIG. 1).

Figure 3A:
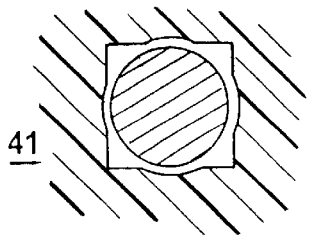
FIGS. 3A and 3B are cross-sectional views taken on respective section lines of FIG. 3.
Figure 3B:
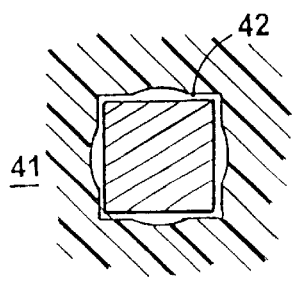

As seen in the cross-section of FIG. 3A the weight is of cylindrical configuration, free to rotate about axis A with turning of the ball to avoid applying drag.

The body portion 12a' of the pin, however, is of square cross-section and is disposed in square channel 42 in spacer block 41 of like configuration to prevent pin rotation so that orientation of end face 12f remains constant. The slope of surface 12f relative to axis A and the flat of square section of the pin are cooperatively related to engage square channel 42. This is accomplished by sloping surface 12f toward a corner of the square channel. Thus micro deposit tip 12d resides at a constant, precisely defined position by cooperation of weight 39, the segment of the conical seat against which the pin is urged by the weight, and by the prevention of pin rotation. Furthermore, by use of a selected weight (instead of a spring), the spotting force upon the substrate is constant over the range of possible heights of the receiving substrate, which in certain circumstances can assure higher repeatability of spot size, than when employing a spring bias system.

Dip & Dot Process

The general concept of a mobile reservoir, shown in our original application is elaborated in FIG. 1 by employing a mobile multi-celled reservoir, MW, such as a multi-well plate. Under computer control, the apparatus brings the appropriate fluid resupply well in alignment under the pin. The pin is then controlled to come down and make contact with the fluid in the reservoir and then raises, taking along a small amount of fluid, in the form of a pendant drop. Under certain circumstances, providing the end of the pin with a tungsten layer or other high surface energy material (surface energy greater than 2500 mN/m) can enhance the transport capability of the pin.

After acquiring its drop, the pin is raised sufficiently to permit the pin and reservoir to separate e.g. by computer controlled sideways movement of the reservoir, such that the pin may subsequently descend unobstructed to deposit the small drop of fluid onto the desired location of the receiving substrate.

It can readily be seen that with appropriate lateral motions of the pin and multi-well supply, this process is repeatable at each location on the substrate where a sample of the selected fluid is desired to be deposited, the desired fluid in the proper well being repeatedly brought into alignment with the proper pin for resupply and later to be deposited in suitable amount in the desired location on the substrate on which the array is being created. Each time a pin is commanded to receive a fluid from a different well than that of its previous command, the pin is moved by computer control to a wash station and processed through a wash cycle to prevent contamination as desired or necessary, e.g. as is disclosed in our first application referred to above.

For efficient operation, a multiplicity of pins may be used advantageously, at spacings matching the pattern of wells so that each pin reaches inside a separate well of the multiple well reservoir such as a "96 well plate" or a "384 well plate".

The pin assembly and its driving mechanisms are preferably mounted on an XY gantry of the instrument as they require the best positional accuracy. The multiple well plate may be provided with two degrees of freedom in a plane parallel to the deposition plane and can be indexed under the pin assembly on a separate structure. Because of the relatively large size of many wells, the translation assembly for the plate may have lower positional accuracy than the pin assembly, especially where cost and mass are to be minimized.

Figure 4:
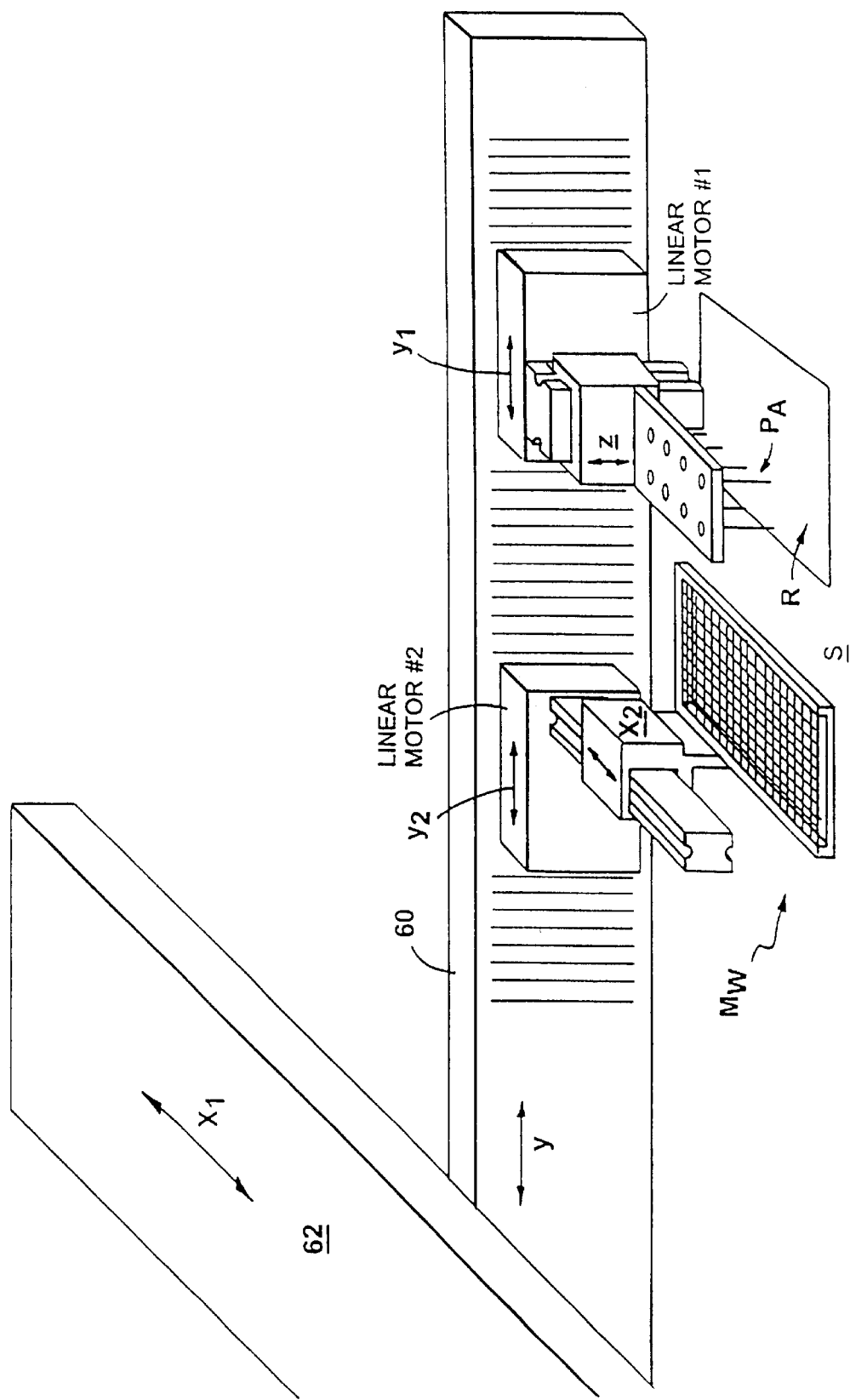
Figure 4A:
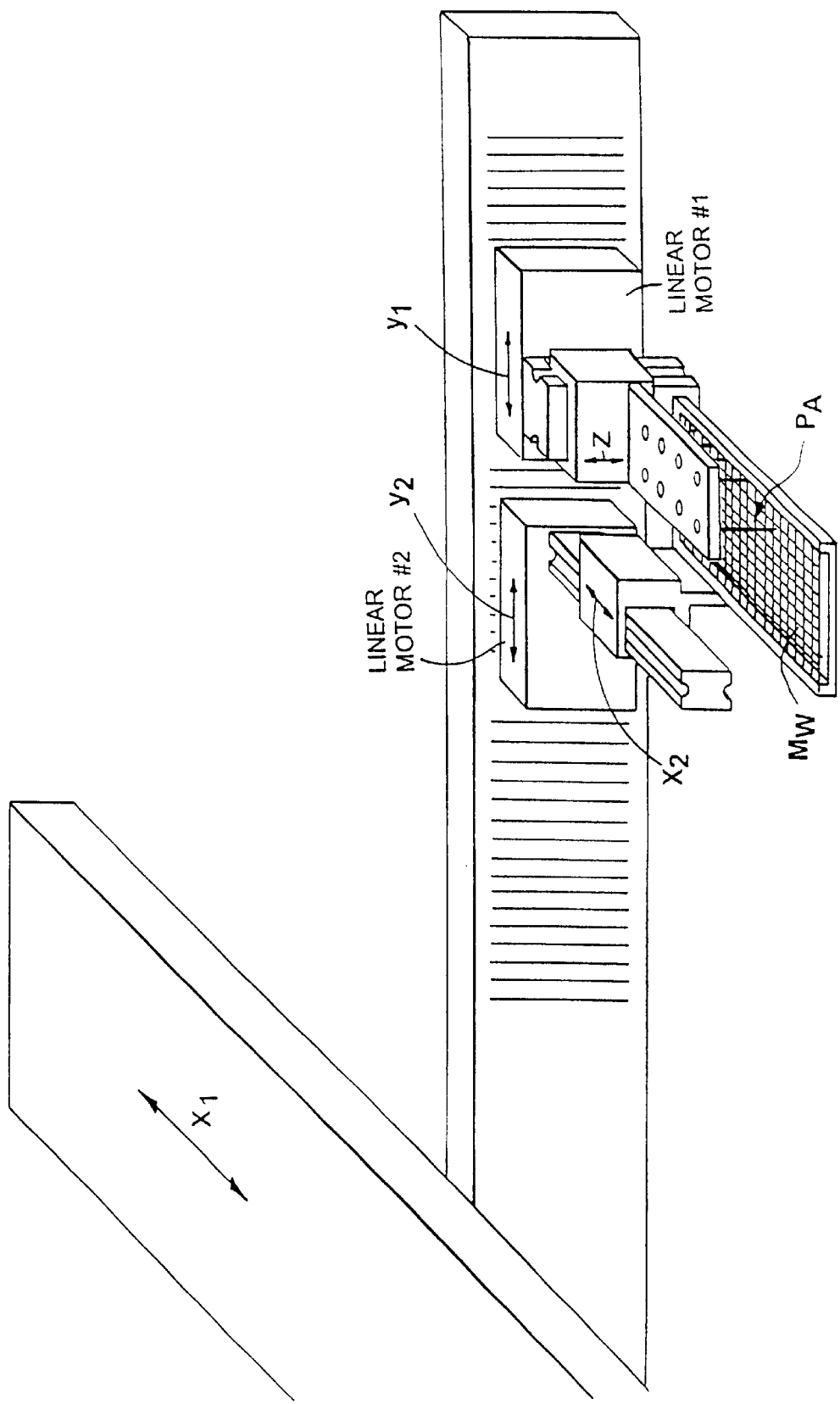
FIG. 4A shows the same elements as FIG. 4 in a supply relationship.

In the embodiment of FIGS. 4 and 4A, however, the multi pin assembly $P_A$ and the mobile multiwell reservoir MW share the same X, Y gantry.

Rail support 60, constructed e.g. to support linear motor movement in the Y coordinate is mounted on an X stage 62, motor not shown. As shown, Y direction linear motors #1 and #2 respectively drive the pin assembly $P_A$ and the multiwell reservoir MW in the Y direction. The reservoir has a secondary linear motor $X_2$ driven by a further driver for relative X movement relative to the pin assembly. The pin assembly also has Z freedom of controlled movement, driven by a further driver Z.

Under computer control, the multiwell reservoir separates in the Y direction from the pin assembly as shown in FIG. 4, and the Z stage is actuated to cause the pins to form deposits upon the substrate S. Then, FIG. 4A, the multiwell reservoir moves under the raised pins into appropriate alignment employing both $Y_2$ and $X_2$ motions under computer control. By Z motion the pins dip into the commanded wells for resupply, the pins rise again, the multiwell reservoir moves laterally with Y motion out of deposition the way and the process is repeated at new targeted X, Y location of the pins. While this mobile reservoir technique is useful with pins of any construction, the advantage of high accuracy of the linear motor indexing system is enjoyed when the pins are constrained in space to a highly accurate repeatable position relative to their carrier, either with the flexure mountings that have been described in our prior applications to which reference is made, or the high density pin arrangements made possible by the structures described with respect to FIG. 13.

Multiple Pin Head Assembly

Figures 5, 6, 7:
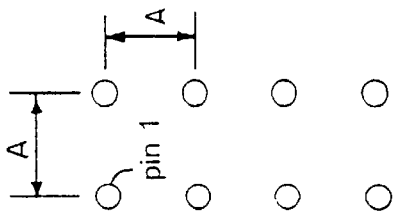
Figure 8:
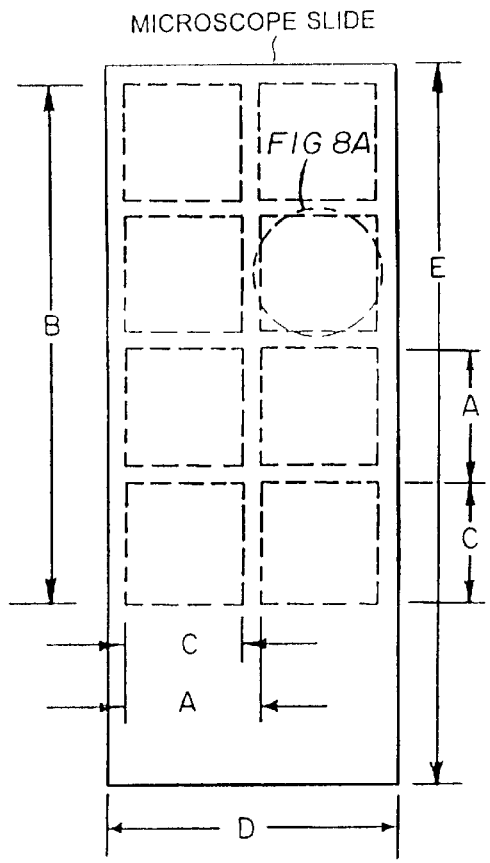
FIG. 8 and FIG. 8A illustrate a pattern of separated squares on a microscope slide which the pins of FIG. 5 can simultaneously address.
Figure 8A:
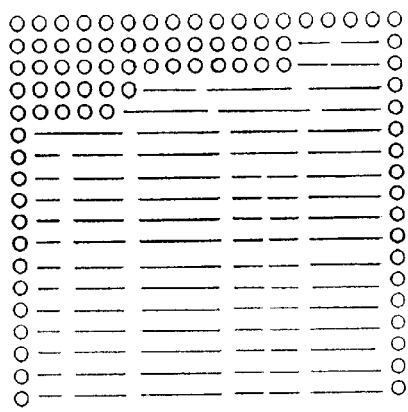

In the preferred embodiment of, FIG. 5, two rows of 4 pins each, preferably constructed according to FIGS. 1–3, are spaced apart in a A=9 mm square grid pattern matching the spacing of the wells of a 96 well plate. Such an arrangement permits the transport of fluid from all 96 wells, 8 wells at a time, and directs the composition of 8 spaced apart blocks of approximate dimension each 8×8 mm, covering in total approximately 18×36 mm sq. One pin deposits in each of 8 squares simultaneously with a single actuation of the Z drive. FIG. 8 shows, in a symbolic manner, the array that has been produced employing the system and method described, wherein A=9 mm, B=36 mm, C=8.5 mm, D=25 mm, and E=75 mm.

Figure 12:
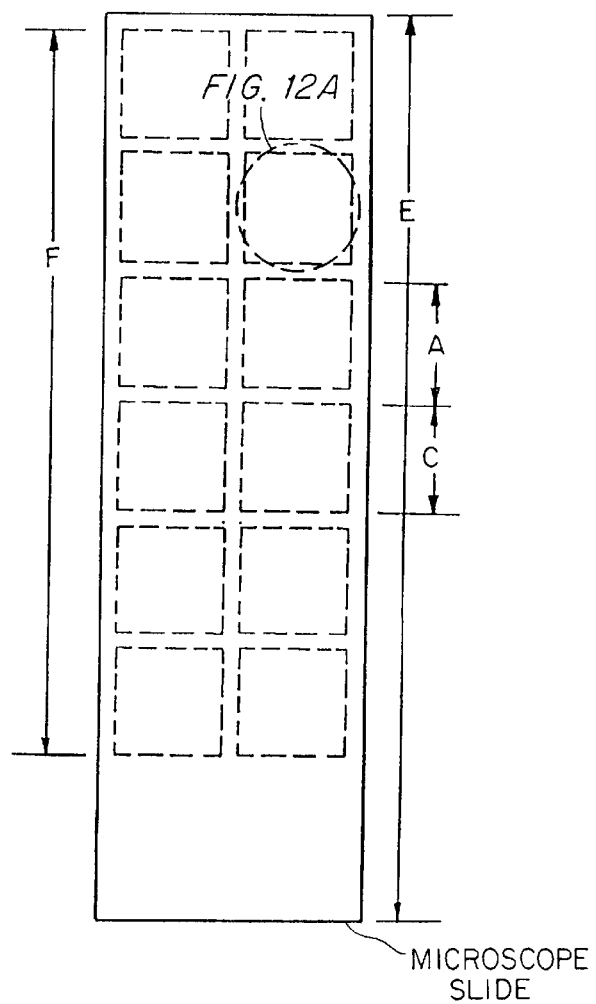
Figure 12A:
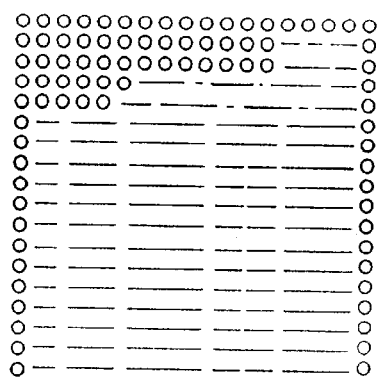

In a similar preferred embodiment, shown in FIGS. 9 and 10, a grid of 12 pins has 2 rows of 6 pins each, again spaced apart in a A=9 mm square grid pattern to match the spacing of the wells of a 96 well plate. This arrangement permits the transport of fluid from all 96 wells, 12 wells at a time, and directs the composition of 12 spaced apart blocks of approximate total area 18×54 mm sq. FIG. 12 shows, in a symbolic manner, such an array, wherein A=9 mm, C=8.5 mm, D=25 mm, E=75 mm and F=54 mm.

The pin assemblage on a 9 mm square grid can also be used to transport fluid from plates with well spacing constructed on a square grid that is based on sub multiples of 9 mm. such as plates with 384 wells or 864 wells or 1536 wells etc. The high accuracy of the computer controlled gantry system enables accurate placement of the selected wells with respect to the pins, and the pins with respect to the receiving substrate.

It is evident that using the same logic, pins can be assembled in denser constructions to fit plates with smaller well spacings.

The benefit of constructions with a large number of pins is that they offer the possibility to create a large number of dots simultaneously on one or many microscope slides or substrates. This can substantially reduce the time and cost required to create arrays.

The denser the array, the tighter the location tolerances for the location of each dot. The flexure pin support described in patent application Ser. No. 09/006,344, filed Jan. 13, 1998, entitled "Depositing Fluid Specimens on Substrates", is useful for individualized action but the system just described is presently preferred for repetitive production of high density arrays. Using these principles, the mode of supplying the tips with fluid can be selected in reference to the nature of the fluid as well as other operating parameters.

In summary, regarding the method aspects of the present invention, FIGS. 5 and 6 illustrate a dipping sequence by which the pattern of a multi-well plate is uniquely transformed to a square pattern on a microscope slide, employing an 8 pin array constructed with a spacing pattern that corresponds with the 9 mm well spacing of a 96 well plate, under computer control to form a much more densely packed array of fluid dots e.g. of 0.25 to 0.025 mm diameter and similar spacing between dots, using all fluids in the plate.

Just as the pins are located on 9 mm centers, the square arrays of high density dots to be formed are themselves spaced on 9 mm centers over the face of the microscope slide. By following the pickup sequence shown in FIG. 7 (rows 1 through 12, and columns A through H) all wells are visited, the pins being conveyed under computer control to the cleaning station, between samplings as shown in connection with FIGS. 16, 16A, 16B, and 17. The contents of the plate are thus distributed from the low density distribution of the wells in a multiwell plate to high density arrays forming parts of the arrays of 8 squares on the microscope slide.

Similarly, referring to FIGS. 9–12, again using 9 mm pin spacing, with two rows of 6 pins each, a sequence of samplings from the wells under computer control collects samples from all wells and distributes them as deposits in 12 squares on a microscope slide with dimensions as shown in FIG. 12.

The Pin & Ring Process

Figure 13A:
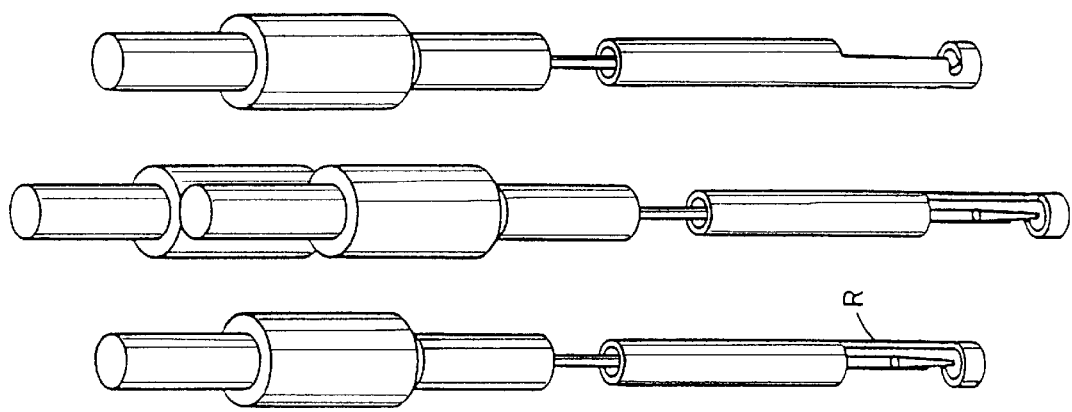
FIG. 13A is a similar view illustrating an array of four such assemblies, which may be mounted for simultaneous actuation by a single driver and may have the number and density of pins expanded, for use with compatible well plates.
Figure 13:
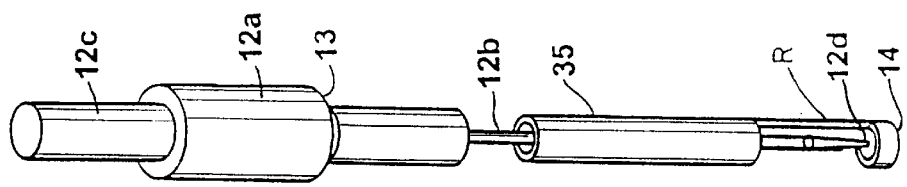
FIG. 13 is a perspective view of an assembled micro deposit pin constructed according to the principles of FIG. 1 combined with a respective supply ring.
Figure 14:
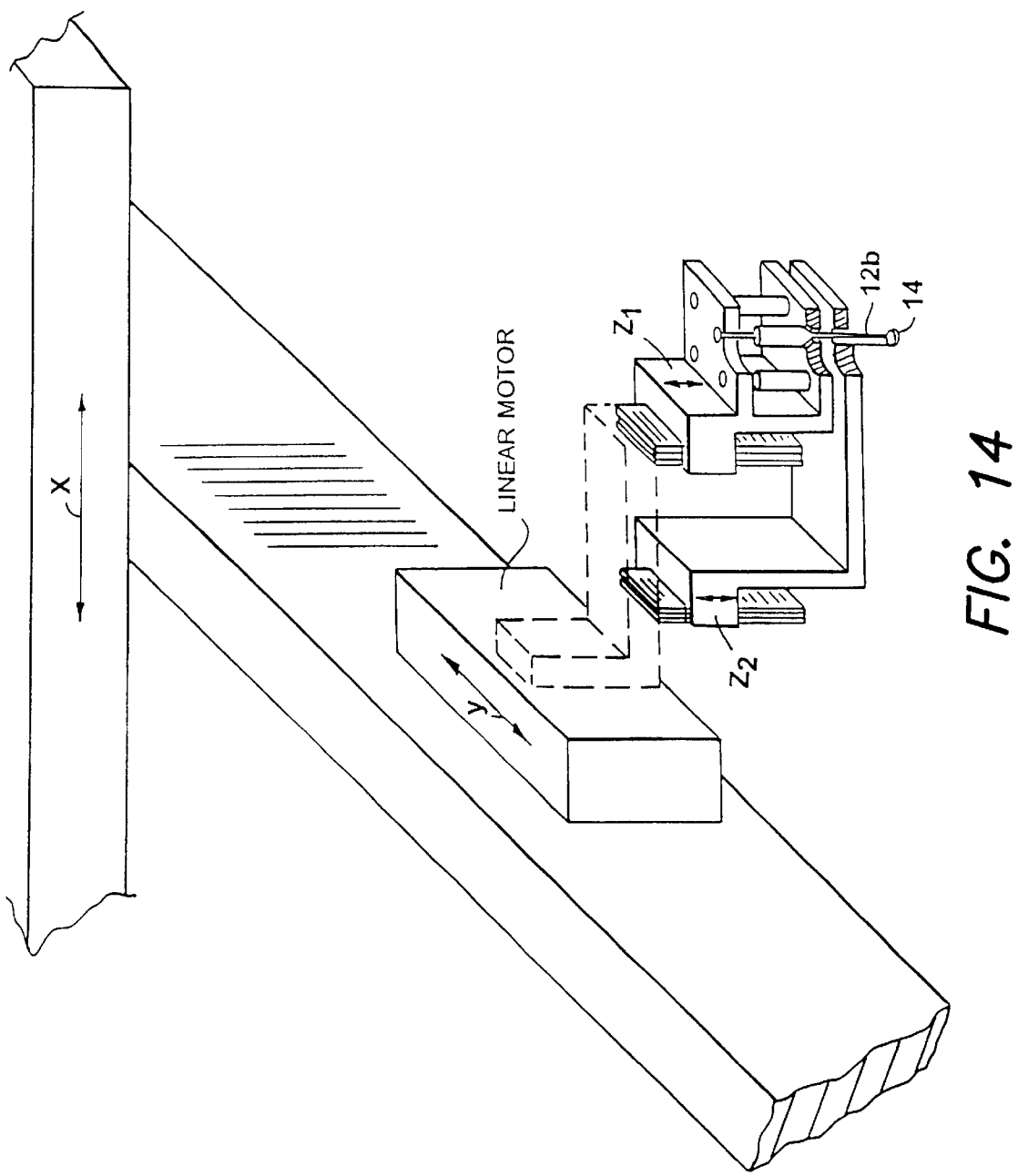

As previously suggested, the same pin assemblies as shown in FIGS. 1–3 can be used with a simple axial ring translation mechanism in a construction analogous to that of the flexure suspension described in our U.S. patent application Ser. No. 09/006,344. As the ring 14 needs to pick up fluid from a rather large well itself, this does not impose a close tolerance requirement, so a compact construction is possible. FIG. 13 shows the relationships of a pin and ring construction without their support or actuation mechanisms. Seen in FIG. 13 are supply ring 14, pin tip 12d, ring body 35 from which a support rod segment R extends to the ring 14, pin shaft 12b, the pin seat 13 formed on pin body 12a and pin guide 12c. FIG. 13A shows a set of such pin and ring assemblies. It is evident that any number can be assembled in this fashion. FIG. 13A depicts a 4 pin and ring assembly where one can see the pin holding structure and the ring holding structure and their respective linear stepper motors $Z_1$, and $Z_2$ that enable relative vertical motion. The respective supporting linear guide rails for X and Y motion are not shown in FIG. 13A, but are shown in FIG. 14 to provide a complete array forming mechanism.

Figure 15:
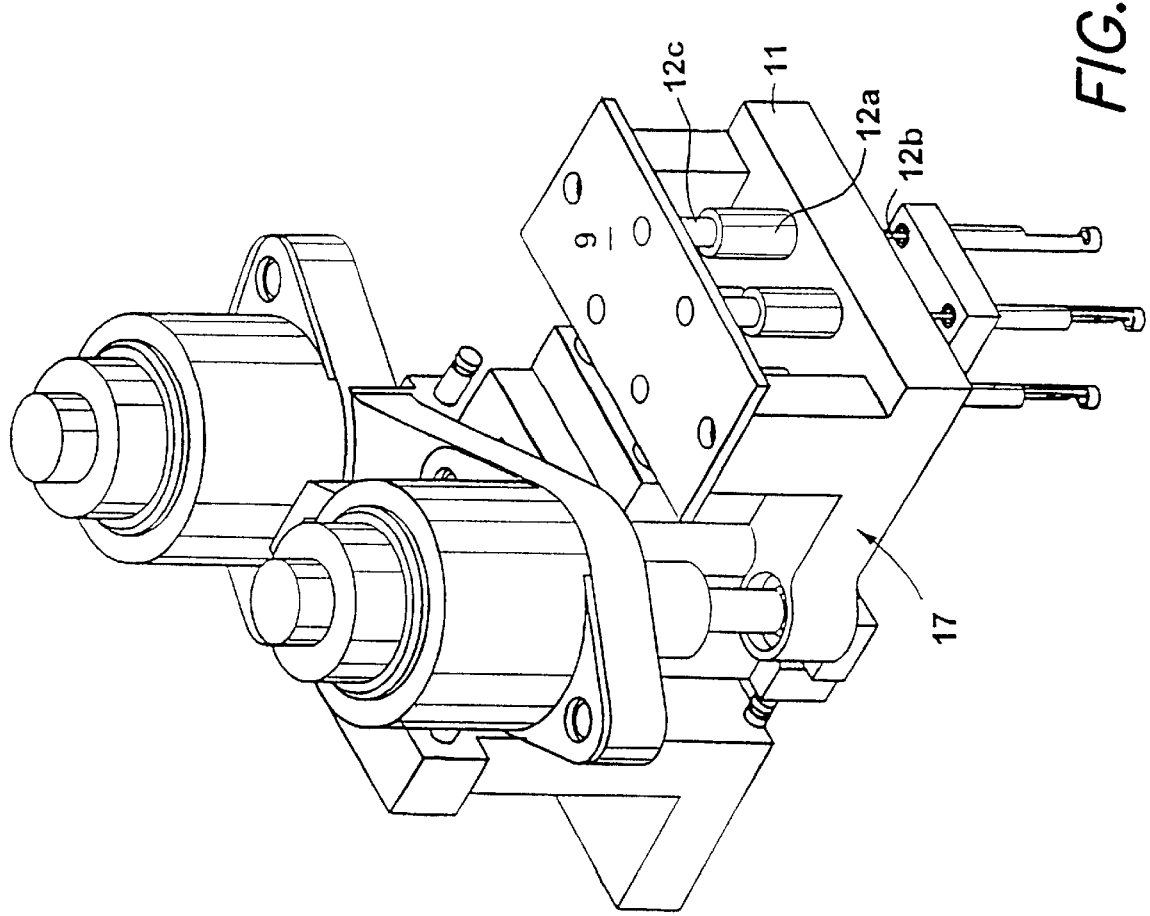
FIG. 15 illustrates an arrayer system, employing the foregoing features, constructed for commercial use.

FIG. 15 illustrates an appealing commercial realization of the design.

As previously mentioned, it is advantageous that surfaces devoted to retaining fluid have a high surface energy, i.e. higher than 2500 millinewton per meter (mN/m), with surfaces comprised of tungsten being presently preferred. In preferred embodiments fluid retention rings 14 are provided with tungsten surfaces in regions where fluid is to be retained preferably the tungsten being provided by electroplating the supply ring, deposit pin of other deposition objects formed of stainless steel. This feature is particularly useful with respect to the storage rings of FIGS. 1, 13–15. By specifically aligning the pin within the ring shown in FIG. 1H, the pin serves as a component of the pickup device, and helps extract the desired fluid in center of very narrow wells, in cases where very little of the fluid is present.

Figure 16:
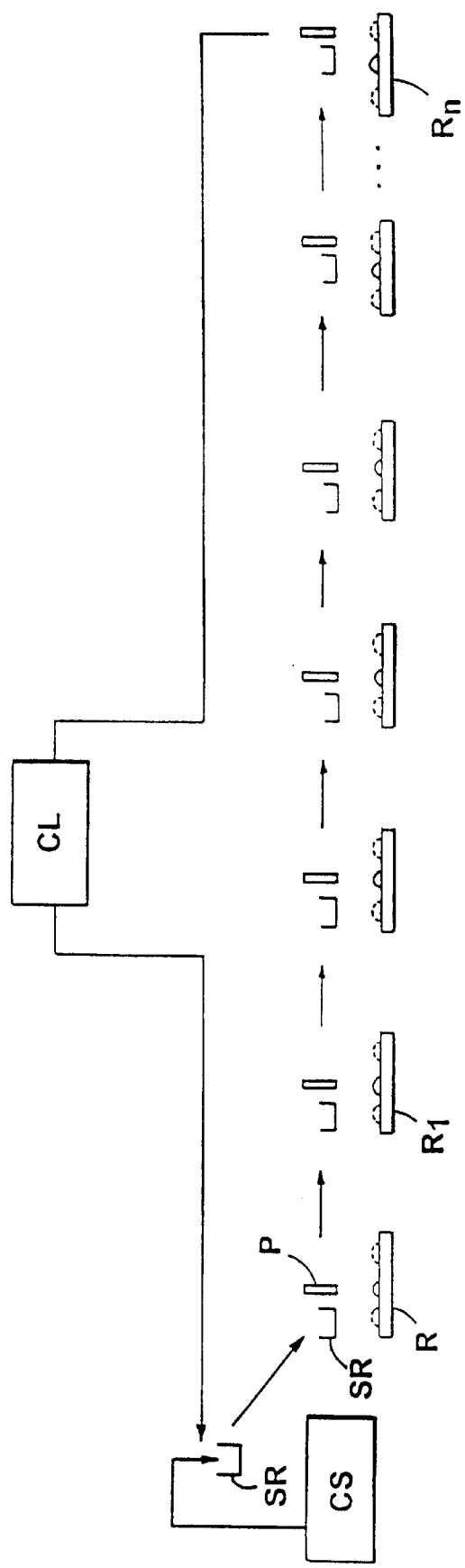
FIG. 16 depicts a system employing the deposition action combined with a cleaning station and central supply of fluid specimen.

The system is especially useful for preparing a number of microscope slides as illustrated in FIG. 16. The central supply CS advantageously is a multiple well plate of a conventional size used in microbiology, such as a 96 well plate. Cleaning and drying stations CL are also provided. The deposit sequence includes moving the assembly of deposit device and mobile sub-reservoir through cleaning and drying stations CL, thence to central supply CS at which the sub-reservoir SR is supplied with a selected fluid sample, e.g. from a selected well in a 96 well plate, under computer control. Thence the grouping moves over a series of receiving surfaces $R-R_n$, for deposit of fluid dots at selected locations on each, also under computer control. This sequence is repeated a number of times, with controlled selection of different fluid samples (from, e.g., the same or different wells of the central supply CS) for respectively different locations on the microscope slides R or other receiving surfaces. Correlation data of respective locations with respective specimens is recorded and used in performing subsequent scanning or reading so that an observed result can be correlated to a given specimen.

Figure 16A:
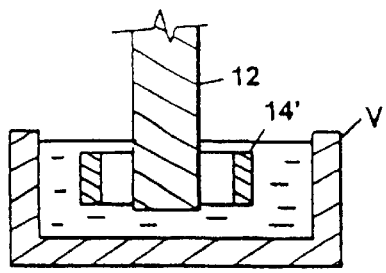
FIG. 16A depicts cleaning the ring and pin at a cleaning station.
Figure 16B:
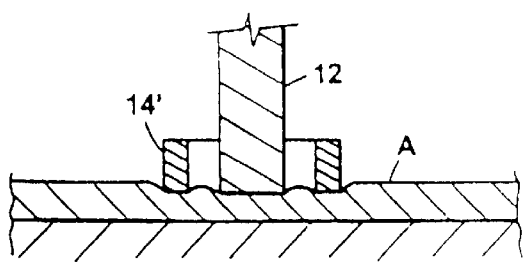
FIG. 16B depicts drying the pin and ring.
Figure 17:
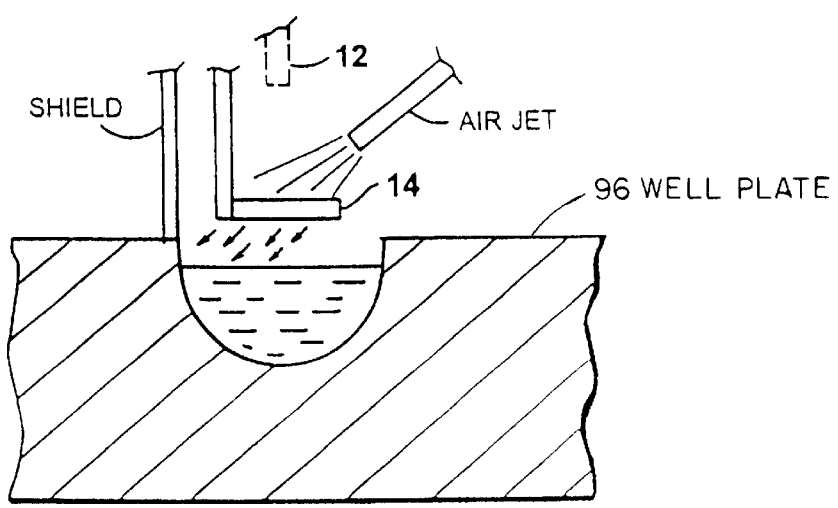
FIG. 17 illustrates a recovery system in which unused fluid is returned to the respective well shown in FIG. 1H.

In the system of FIG. 4, the array of pins and rings of a cluster may be held over a vessel of water for cleaning, as shown in FIG. 16A. The vessel has water level and a pump constantly stirs the water. Also associated in FIG. 16B is a tile of blotting paper or in some implementations, a cellulose sponge. In operation, following washing, the array of four ring and pins are touched upon the blotting paper for drying.

The X, Y control of the system of FIG. 4 can accurately position the devices so they contact fresh areas of the blotter each time. The computer keeps track of the positions that have been used and guides the deposit head to new positions.

After the deposition sequence is complete, the X and Y terminal drives the cluster of depositing elements to the cleaning station. In some embodiments they may be passed over the wells from which the fluid originated and subjected to air blast, see FIG. 17 or by abrupt stopping of rapid downward movement to return excess fluid to the wells. At the cleaning station the depositing elements are positioned over a clean part of the blotting paper or sponge, FIG. 16B, and then both the pins and the rings are driven to contact the sponge. With a small application of force the parts catch up with each other and become co-planar. After a short interval the fluid is wicked from the rings and pins. Then the multiplicity of devices is lifted and thrust into the container of water, FIG. 16A. The water is constantly agitated and the devices are exposed to substantially fresh water as they are being rinsed. The main servo system of the X or Y axis can be employed to move the rings and pins e.g. in swirling motion to effect stirring or agitation. The deposit pins and the rings are then lifted from the water tray, FIG. 16A, and brought to the blotting tray or a fresh blotting tray where the rinse water is blotted from the rings and pins to provide substantially dry devices for the next fill and deposit cycle.

These enumerous other specific arrangements employing principles as we have outlined here will be understood from the text, the drawings and the following claims taken in conjunction with our prior applications which have been incorporated by reference.

What is claimed is:

1. A fluid deposit assembly mounted on a carrier for depositing minute drops of fluid at selected locations upon a substrate for creating a dense array of biological objects, comprising:
    a deposit device comprising
        a deposit element having a diameter of 0.3 mm or less constructed and arranged to carry and deposit drops of fluid upon the substrate,
        stable lateral reference surfaces or surface portions exposed for engagement by the deposit element, the surfaces or surface portions being constructed and arranged to prevent X, Y displacement of the deposit element relative to the carrier when the deposit element is urged thereagainst,
        means for urging the deposit element substantially laterally against the reference surfaces or surface portions at least at the time that the deposit element approaches a substrate to deposit a fluid drop, the reference surfaces or surface portions and the means for urging cooperating to precisely position the deposit element in a precisely desired position as it contacts the substrate; and
    a mobile local device, comprising a surrounding surface cooperatively arranged with and larger than the deposit element, for limiting evaporation of the fluid at the deposit element.

2. The fluid deposit assembly of claim 1 in which the deposit element is the tip of an axially moveable pin.

3. The deposit assembly of claim 2 in which the means for urging comprises a spring having spring portions selected to provide compliance to the tip of the pin.

4. The deposit assembly of claim 3 in which the spring provides at least in part the pressure with which the pin bears upon the substrate.

5. The deposit assembly of claim 1 or 2 in which the means comprises an arrangement of the assembly so that gravity effects cause the deposit element to engage the reference surfaces or surface portions.

6. The deposit assembly of claim 5 in which the deposit device is tilted in a manner by which gravity acting upon the device produces the engagement.

7. The deposit assembly of claim 5 in which an eccentric weight acts through the device to maintain the engagement.

8. The deposit assembly of claim 1 or 2 in which the reference surface portions comprise a surface of revolution whose axis is disposed at a predetermined position relative to the carrier.

9. The deposit assembly of claim 8 in which the surface of revolution is in the form of a circular supporting ledge that supports the element from moving in its assembly in the direction toward the substrate, but from which the element is free to lift off in response to contact of the tip with the substrate as the ledge and elongated element are together moved relatively toward the substrate.

10. The deposit assembly of claim 9 in which a resilient member urges the deposit element into engagement with the surface of revolution.

11. The deposit assembly of claim 10 in which the surface of revolution is of concave curvature and a mating surface of the deposit element is of convex curvature.

12. The deposit assembly of claim 9 in which the surface of revolution has a surface of form substantially matching the form of the portion of the element disposed to engage the surface of revolution.

13. The deposit assembly of claim 12 in which the matching surfaces are respectively concave and convex conical.

14. The deposit assembly of claim 8 in which the reference surface portions comprise a conical surface included in the carrier and a spherical surface included in the deposit element substantially axially.

15. The deposit assembly of claim 1 or 2 in which the means applies a turning moment on the deposit element.

16. The deposit assembly of claim 15 in which the deposit element is elongated, the moment is applied by a pushing member engaged with a remote end of a deposit element, one of the engaged end and pushing surfaces comprising a surface set at an acute angle to the long axis of the elongated element, and the other of the surfaces comprising a convexly curved surface engaged upon the angled surface.

17. The deposit assembly of claim 16 in which a confined ball is pushed toward the inclined surface.

18. The deposit assembly of claim 1 or 2 in which a formation on a part of the deposit element engages a mating formation on the carrier to prevent rotation of the element about its axis.

19. The deposit assembly of claim 1 in which the end of the deposit tip is of substantially square side profile adapted to carry fluid by surface tension effects.

20. The apparatus of claim 1 in which the deposit element includes a tip of a moveable deposit pin and a mobile local device includes a member which defines a generally annular fluid retention surface being significantly larger than the tip, and the deposit pin is constructed to move within the annular retention surface from retracted to extended positions, in the retracted position the deposit end of the pin being retracted from the lower surface of fluid retained by the annular surface of the storage device, and in the extended position the deposit end of the pin being projected beyond the lower surface of the retained fluid.

21. The apparatus of claim 20 in which the annular surface is aligned with the pin and a driver is associated with the member that defines the annular surface to move the member generally linearly downwardly beyond a position of a deposit end of the pin to a replenishment position, the pin and the member defining the annular surface and associated drivers being movable to the cleaning system, and to a replenishment region in which the annular member is replenished.

22. A deposit assembly for creating a dense array of biological objects, comprising:
a multiplicity of deposit devices each including a deposit element arranged to carry and deposit drops of fluid, lateral reference members constructed to define X and Y positions of said deposit elements when contacting a substrate for deposition of said fluid, said multiplicity of deposit elements being mounted for motion together, in response to a common actuator, near deposition locations on said substrate, and
a multiplicity of local mobile reservoirs co-operatively constructed and arranged with said multiplicity of deposit devices to provide said drops of fluid to said deposit elements by relative substantially vertical motion, said mobile reservoirs being constructed to travel near said deposit locations for providing said drops of fluid to said deposit elements.

23. The deposit assembly of claim 22 wherein each said local mobile reservoir comprises a ring, each said deposit element includes a tip of a deposit pin, said tip having a lose fit for axial movement without being in contact with said ring.

24. The deposit assembly of claim 21 comprising a predetermined multiwell plate having a selected spacing of wells, each said well being constructed to receive said ring.

25. The assembly of claim 24 in which the spacing corresponds to a well-to-well spacing of wells of a 96, 384, 864 or 1536 well plate and said multiplicity of rings has a corresponding fixed spacing designed for insertion inside said wells.

26. The assembly of claim 23 wherein the ring has a surface energy greater than about 2500 mN/m for providing said drops of fluid to said deposit elements.

27. The assembly of claim 26 in which the surface comprises tungsten.

28. The assembly of claim 20 wherein said local mobile reservoirs are constructed to accompany the deposit device across the substrate and to move sideways after providing said drops of fluid to enable unobstructed deposition of said drops of fluid by said deposit elements onto said substrate.

29. The assembly of claim 1 or 28 in which the deposit element has a tip with a surface energy greater than about 2500 mN/m.

30. The assembly of claim 1 or 28 in which the surface of the tip of the deposit element comprises tungsten.

31. An apparatus for deposit of fluid samples in a dense array of mutually isolated dots, comprising
a deposit device comprising multiple deposit pins movable relative to the deposit device, each said deposit pin having a tip of a diameter of 0.3 mm or less constructed and arranged to carry and deposit drops of fluid upon a substrate; the deposit device and the deposit pin comprising stable lateral reference surfaces or surface portions constructed and arranged to prevent an X and Y displacement of the deposit element and an urging mechanism for providing a substantially vertical force onto the deposit pin;
a mobile fluid storage including a fluid source for repeatedly providing a discrete drop of fluid on the tip of the deposit element of the device, the mobile fluid storage and the deposit pins being cooperatively arranged for each tip to receive the drop of fluid by surface tension;
a mechanism for moving the deposit device relatively over an array of spaced apart deposit locations of a receiving substrate, and a mechanism for repeatedly moving the deposit element, relatively, toward and away from the substrate to deposit respective dots at respective deposit locations on the substrate.

32. The apparatus of claim 31 including a cleaning system, and a control system adapted to control relative movement of the deposit device to a depositing relationship to the substrate and a cleaning relationship to the cleaning system.

33. The apparatus of claim 31 wherein the mobile fluid storage repeatedly moves to resupply the deposit tips during the deposit of successive dots.

34. The apparatus of claim 31 in which the mobile fluid storage is a mobile local fluid storage device separate from the deposit device and generally movable over the array of deposit locations, the mobile fluid storage being constructed and arranged to resupply the deposit tip at various locations with respect to the array.

35. The apparatus of claim 31 further including a mobile local fluid storage device constructed for immersion into the mobile fluid storage to receive the fluid, and wherein the pin is constructed and arranged to dip into a volume of fluid carried by the mobile local storage device and to project through the volume of fluid for deposition of the dot at the substrate.

36. The apparatus of claim 35 in which the mobile local storage device includes a multiplicity of rings is constructed to store a multiplicity of isolated fluid volumes, the apparatus being constructed to move the mobile local storage device relative to the deposit device to provide the fluid to be deposited.

37. The apparatus of claim 35 in which the mobile fluid storage is a plate having 96 wells or multiples of 96 wells.

38. The apparatus of claim 37 including a driven stage for moving the multiwell plate into registry with the deposit device under computer control for enabling dipping of the deposit device into a preselected well of the plate and away from the deposit device, from the device to enable the device to make its deposit.

39. A method of producing arrays of fluid dots comprising the acts of:
providing an array of deposit pins having pin spacing comparable with the well spacing of a 96 well plate, or a plate having a multiple of 96 wells;
moving the well plate toward a substrate and the array of pins;
dipping the pins into wells of the well plate to receive fluid by surface tension;
causing a relative lateral movement of the well plate and the array of pins; and
transferring the fluid from tips of the respective pins to respective dot locations in a substantially denser array on the substrate.

40. The method of claim 39 further including providing an array of rings, each ring surrounding one said pin, and wherein the act of dipping the pins into the wells includes lowering the ring inside the well.

41. The method of claim 40 wherein the act of transferring the fluid from the tips of the pins includes lowering the tips through the rings in a manner that a drop of the fluid adheres to the tip by surface tension.

42. An array product comprising deposited dots of fluid in a dense array of biological objects corresponding to a function of the distribution of wells of a 96 well plate, the array product being created by providing a deposit array of pins having a spacing comparable with the well spacing of the 96 well plate; moving the well plate toward a substrate and the array of pins; dipping the pins into wells of the well plate to receive fluid by surface tension; causing a relative lateral movement of the well plate and the array of pins; and transferring the fluid from tips of the respective pins to respective dot locations to create a substantially denser array on the substrate.

43. An apparatus for creating a dense array of biological objects, comprising a mobile local fluid storage device separate from a deposit device and movable therewith over an array of deposit locations, the mobile local fluid storage device being constructed and arranged to be immersed into a fluid storage and subsequently re-supply the deposit device at various locations with respect to the array.

44. The apparatus of claim 43 in which the mobile local storage device is constructed to store a multiplicity of isolated fluid volumes, the apparatus constructed to move the local storage device relative to the deposit device to select the fluid to be deposited.

45. The apparatus of claim 44 in which the deposit device is a pin constructed and arranged, under computer control, to dip into a selected volume of fluid carried by the mobile local storage device.

46. The apparatus of claim 44 in which the fluid storage is a plate having 96 wells or multiples of 96 wells.

47. The apparatus of claim 46 including a driven stage for moving the multiwell plate into registry with the deposit device under computer control for enabling dipping of the device into a preselected well of the plate and away from the device to enable the device to make its deposit.

48. A method of causing a biological compound to interact with another substance at a predetermined position on a substrate or to build up on that substrate the step comprising
providing a deposit device including a deposit pin, movable relative to the deposit device, constructed and arranged to carry and deposit drops of fluid upon a substrate; the deposit device and the deposit pin comprising stable lateral reference surfaces or surface portions constructed and arranged to prevent an X and Y displacement of the deposit pin and an urging mechanism for providing a substantially vertical force onto the deposit pin;
providing the compound or reagent to a mobile fluid storage;
depositing at least one of the compound or reagent in a precisely determined localized spot relative to the substrate by mechanically lowering the pin to which a drop of the compound or reagent is adhered by surface tension from the mobile fluid storage, toward the substrate until the drop contacts the substrate or a pre-applied compound on the substrate with the pin exerting a controlled force of less than a gram thereon, and thereafter mechanically lifting the pin away from the substrate under conditions in which the fluid drop transfers to the substrate or the pre-applied compound on the substrate.

49. The method of claim 48 in which drops of both the compound and the other substance are successively deposited by the technique of claim 46.

50. The method of claim 48 in which the pin, when approaching the substrate, applies a force to the substrate with a force of about 0.5 grams.

51. The method of claim 48 in which a supply of the biological compound or substance to be deposited by the pin is supported above the substrate at the deposit location within a ring by surface tension, the ring being part of the mobile fluid storage, and the pin is lowered through the ring in the manner that a relatively small drop of the reagent from the supply is adhered to the end of the pin by surface tension.

52. The method of claim 48 in which the fluid to be deposited from fluid selected from a group of fluids disposed in a mobile multiwell plate, included in the mobile fluid storage, that moves across the substrate to be in proximity to the deposit pin.

53. The method of claim 52 in which the multiwell plate includes a cleaning agent or a cleaning station.

* * * * *